US008968676B2

(12) United States Patent
Porsch et al.

(10) Patent No.: US 8,968,676 B2
(45) Date of Patent: Mar. 3, 2015

(54) METHOD OF MEASURING AN ANALYTE CONCENTRATION IN A SAMPLE OF A BODY LIQUID

(71) Applicant: Roche Diagnostics Operations, Inc., Indianapolis, IN (US)

(72) Inventors: Ulrich Porsch, Weinheim (DE); Bernd Steiger, Roemerberg (DE); Gertrud Albrecht, Mannheim (DE); Uwe Wittmann, Lampertheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 14/273,661

(22) Filed: May 9, 2014

(65) Prior Publication Data

US 2014/0249778 A1    Sep. 4, 2014

Related U.S. Application Data

(63) Continuation of application No. 13/116,061, filed on May 26, 2011, now abandoned, which is a continuation of application No. PCT/EP2009/008048, filed on Nov. 12, 2009.

(30) Foreign Application Priority Data

Dec. 2, 2008  (EP) ..................... 08020879

(51) Int. Cl.
*G01N 33/00* (2006.01)
*G06F 19/24* (2011.01)
*A61B 5/145* (2006.01)
*G01N 33/487* (2006.01)
*G06F 19/00* (2011.01)

(52) U.S. Cl.
CPC ............ *G06F 19/24* (2013.01); *A61B 5/14532* (2013.01); *G01N 33/48764* (2013.01); *G06F 19/3412* (2013.01)
USPC ............................ 422/403; 422/404; 422/68.1

(58) Field of Classification Search
USPC .......................................... 422/403, 404, 68.1
See application file for complete search history.

(56) References Cited

U.S. PATENT DOCUMENTS 6,600,997 B2    7/2003  Deweese et al.
2005/0103351 A1    5/2005  Stomberg et al.

FOREIGN PATENT DOCUMENTS

| DE | 197 33 445 A1 | 2/1999 |
| EP | 1 801 718 | 6/2007 |
| EP | 1 987 766 | 11/2008 |
| WO | WO 2007/030457 | 3/2007 |

OTHER PUBLICATIONS

Malcolm W. Stevens, Unification of Relative Time Frames for Digital Forensics, Digital Investigation, 2004, pp. 225-239, Copyright 2004 Published by Elsevier Ltd.

*Primary Examiner* — Sam P Siefke
(74) *Attorney, Agent, or Firm* — Roche Diagnostics Operations, Inc.

(57) ABSTRACT

A hand-held device for measuring an analyte concentration in a sample of a body liquid includes a display means for displaying measured values; a measured-value storage for storing measured values; a measuring unit for generating measured values through measurements of the analyte concentration; a clock; a control unit for generating measured value datasets, each containing a measured value supplied by the measuring unit as well as the date and hour of the measurement by which the measured value was obtained, and for writing them into the measured-value storage; and operating elements that can be actuated by the user to set the clock, in which case the control unit will generate a time-correction dataset indicating the amount and direction of the setting effected. The control unit writes time-correction datasets into the measured-value storage so that a chronologically ordered sequence is generated containing time-correction datasets and measured value datasets.

13 Claims, 1 Drawing Sheet

| A | B | C | D | |
|---|---|---|---|---|
| 0122 | 1243 | 081120 | 0021 | ← M1 |
| 9999 | 0120 | 000000 | 00B1 | ← T |
| 0083 | 2031 | 081120 | 0033 | ← M2 |
| 0154 | 0802 | 081121 | 1010 | ← M3 |

METHOD OF MEASURING AN ANALYTE CONCENTRATION IN A SAMPLE OF A BODY LIQUID

CROSS-REFERENCE TO RELATED APPLICATIONS

This application is a continuation of U.S. patent application Ser. No. 13/116,061 filed on May 26, 2011, which is a continuation of International Application No. PCT/EP2009/008048 filed Nov. 12, 2009, which claims priority to EP Application No. 08020879.6 filed Dec. 2, 2008. Each of the referenced applications is incorporated herein by reference in its entirety.

FIELD OF THE INVENTION

The present invention relates to a hand-held device for measuring an analyte concentration in a sample of a body liquid.

BACKGROUND

A hand-held device for measuring an analyte concentration has been known from WO 2007/030457 A1 and is used for quantitative analysis of body liquids, for example of urine, blood and interstitial liquid, i.e. for measuring the concentration of medically significant analytes such as lactate, cholesterol and, especially, glucose.

Hand-held devices of that kind can be carried along by the users and are needed, for example, by diabetics who are required to measure their glucose concentration on a sample of blood and/or interstitial liquid several times a day.

The measured values so obtained can be stored in a measured-value storage of the hand-held device for being transferred later to an external evaluation unit, for example a physician's PC. By evaluating the measured values obtained over an extended period of time it is possible to optimize the medical treatment of chronic diseases such as diabetes. Modern hand-held devices therefore comprise a clock so that when the measuring results are evaluated later the development over time of the analyte concentration can be examined in relation to a stored time information.

The time-dependent relation between the different measured values may be distorted when the setting of the clock is altered. This can be avoided when the hand-held device is equipped with an internal clock that cannot be set by the user, a system that has been known from DE 197 33 445 A1. Given the fact that medically relevant analyte concentrations normally are subject to variation according to the rhythm of the day it is, however, desirable to provide the clock of a hand-held device with a setting function so as to allow the time of the day to be adjusted between summer time and winter time or on travels between different time zones. In order to ensure that the evaluation of measured values obtained over an extended period of time will not be distorted, it is necessary that such time adjustments be recorded.

WO 2007/030457 discloses a hand-held device where measured values, as well as the date and hour of the measurement by which the respective value was obtained, are combined to form measured-value datasets which are continuously stored in a measured-value storage. When the clock is set, the amount and direction of the change is stored in a storage (buffer log) provided for that purpose so that the respective information can be taken into account in evaluating the measured values later.

SUMMARY

The present invention shows a way how a sequence of measured values of a hand-held device can be evaluated with little input and without being falsified by alterations of the time setting that may have been made.

The invention includes a hand-held device for measuring an analyte concentration in a sample of a body liquid comprising: a display means for displaying measured values; a measured-value storage for storing measured values; a measuring unit for generating measured values through measurements of the analyte concentration in samples of a body liquid; a clock for supplying the date and hour of the day; a control unit for generating measured value datasets, each containing a measured value supplied by the measuring unit as well as the date and hour of the measurement by which the measured value was obtained, and for writing them into the measured-value storage; operating elements that can be actuated by the user to set the clock, in which case the control unit will generate a time-correction dataset indicating the amount and direction of the setting effected, wherein the control unit writes time-correction datasets into the measured-value storage so that a chronologically ordered sequence is generated containing time-correction datasets and measured value datasets.

Every time the clock is set, the hand-held device generates a time-correction dataset that indicates the amount and direction of the setting and is stored in the measured-value storage of the hand-held device together with measured value datasets containing each a measured value as well as the information on the date and hour the dataset was generated. Accordingly, a chronological sequence made up from the time-correction datasets and the measured-value datasets is generated in the measured-value storage of a hand-held device according to the invention. The time-correction datasets and the measured-value dataset are therefore sorted in the measured-value storage according to the time of generation of the respective dataset. This provides several advantages:

A single storage suffices for a hand-held device according to the invention. Thus it possible to save components and related production costs.

The clock of a hand-held device according to the invention can be set almost as often as desired, the number of time-correction datasets that can be stored between measured-value datasets of a series of measured values being limited only by the size of the measured-value storage.

The position of a time-correction dataset within a series of measured value datasets defines unambiguously the measured-value dataset to which the respective time-correction dataset relates. The exact time, i.e. the date and hour, of a setting effected will not be required later for evaluation and, accordingly, does not need to be recorded or stored so that the time-correction datasets of a hand-held device according to the invention can be given a very simple structure. The storage position of the time-correction dataset within the measured-value storage, together with the amount and direction by which the clock was adjusted, are sufficient to permit correct evaluation of a series of measured-value datasets.

Given the fact that time and time-correction information do not have to be evaluated in the hand-held device, a hand-held device according to the invention can be equipped with a very simple and, therefore, cost-effective control unit. A series of datasets in chronological order can be retrieved by an external device from the measured-value storage of the hand-held device without any difficulty via a hardware interface, and can be evaluated at any time, all relevant information being contained in the chronologically sorted sequence of datasets.

The evaluation can be restricted to any desired fraction of the chronologically sorted sequence of measured-value datasets and time-correction datasets. For, the time-dependent relation between a desired number of successive measured value datasets is clearly documented by time-correction datasets placed between them so that any desired partial series of datasets can be correctly evaluated without any additional information being needed. This facilitates the use at a later time and the repeated evaluation of data, that were obtained by a hand-held device according to the invention, by an external device, for example a physician's PC.

In the event of a partial loss of data the remaining part of the data do not become worthless as the evaluation can be limited to any desired number of successive data set.

An advantageous further development provides that the measured value datasets and the time-correction datasets have the same length. This helps simplify the architecture and management of the measured-value storage as all strings to be stored as datasets in the measured-value storage have the same length.

Time-correction datasets and measured value datasets can be distinguished for example by a special data field or a flag. In one embodiment, the time-correction datasets are identified as such by a marking that begins, related to the beginning of the dataset, in the same position in which a field containing the measured value begins in a measured value dataset. It is possible in this way to give the datasets an advantageously short length as no additional field is required for differentiation. This is so because the marking envisaged by the invention may, for example, include a string of characters or bits which, in a measured-value field of a measured value dataset, would represent a value that would be impossible physiologically. According to one embodiment, the marking may include a character string that begins by the digit 9, especially by 99.

Having the marking begin with a string representing the digit 9 makes it possible, for example, to use the bit string 99 or 999 as a marking for a time-correction dataset in a data field which, in a measured value dataset, would contain a measured value, as corresponding concentration values will never be encountered in practice.

It is further contemplated to give the markings of the time-correction datasets the same length as the field of the measured value datasets that contains the measured value. Even though two digits 9, followed by any third digit, would be sufficient in the described example as a marking for a time-correction dataset, a greater number of characters or digits would provide improved safety from writing or reading errors.

In addition, the marking identifying time-correction datasets as such can be positioned at the beginning of a time-correction dataset. This permits time-correction datasets to be recognized as such.

BRIEF DESCRIPTION OF THE FIGURES

Further details and advantages of the invention will be described hereafter with reference to one embodiment and to the attached drawings. In the drawings.

DETAILED DESCRIPTION

Figures 1, 2:
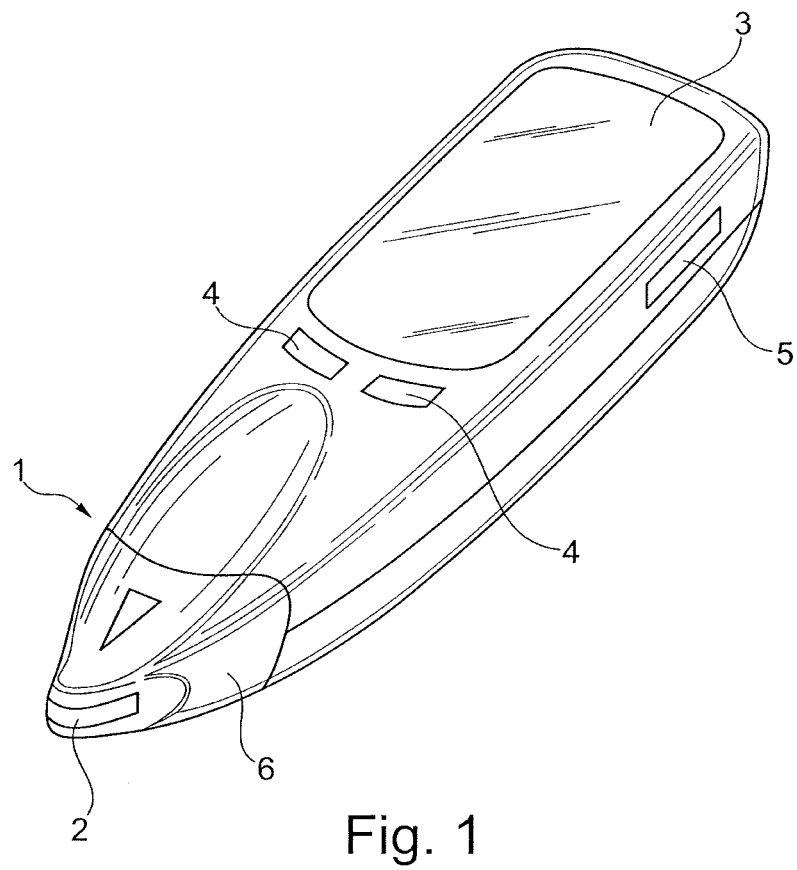
FIG. 1 shows an embodiment of a hand-held device according to the invention.
FIG. 2 shows the data structure of the datasets generated by the hand-held device.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and such further applications of the principles of the invention as illustrated herein are contemplated as would normally occur to one skilled in the art to which the invention relates.

FIG. 1 shows an embodiment of a medical hand-held device 1 for determination of an analyte concentration in a sample of a body liquid of a person or an animal. In the illustrated embodiment, the hand-held device 1 is a glucometer, intended to be used by diabetics for determination of the glucose concentration in a sample of blood or interstitial fluid.

For measuring, a sample of a body liquid is applied onto a test field section of a carrier strip 2, and following a transport step of the strip of suitable length the analyte concentration in the sample so applied is measured in the device 1 by a measuring unit, for example photometrically or electrochemically. There is also the possibility to configure the hand-held device 1 in such a way that a concentration can be determined with the aid of a consumable material in the form of test strips. Test elements may be stored for example in a magazine in the device, or can be introduced together with the sample applied through an opening in the housing. For loading fresh consumable material, for example a cassette containing carrier strip 2, or for replacing batteries in a battery compartment, a housing part 6 is made detachable.

Measuring results of the analyte concentration are displayed by a display means 3, preferably a liquid crystal display, for example a segment display. The measured values so obtained may be displayed together with an indication of the date and hour, which may be supplied by a clock integrated in the hand-held device 1. A control unit of the hand-held device 1, such as a microprocessor, generates from a measured value and from the date and hour of the respective measurement a measured value dataset and writes it into the measured-value storage which can be read out by an external device via a hardware interface 5.

In the illustrated embodiment, the hardware interface is designed for plug-in connection. There is, however, also the possibility to design the hardware interface for wireless data transmission.

Operating elements 4 that can be actuated by the user are provided for operation of the device 1 and, especially, for setting the clock. When the integrated clock is set, the control unit of the device 1 generates a time-correction dataset, defining the amount and direction of the setting, and writes that dataset into the measured-value storage so that a chronologically ordered sequence of time-correction datasets and measured value datasets is generated in the measured-value storage. The chronological order relates to the point in time at which the respective dataset was generated and is derived automatically due to the fact that the datasets are stored in the measured-value storage simply one after the other.

FIG. 2 shows the structure of the datasets so stored in the measured-value storage. The illustrated detail is a diagrammatic representation of four successive datasets M1, T, M2 and M3, representing a section of a sequence stored in a measured-value storage. The datasets M1, M2 and M3 are measured value datasets, the record T is a time-correction dataset. The dataset M1, M2, M3 and T all have the same length and contain four data fields A, B, C, D.

The first data field A has a length of four characters and contains, in the case of the measured value datasets M1, M2, M3, a measured value of a glucose concentration, for example in mg/dl. With respect to the time-correction dataset T the data field A contains the entry 999 which identifies it as a time-correction dataset.

The second data field B also has the length of four characters and indicates, in the case of the measured value datasets M1, M2, M3, the hour of the day at which the measurement was taken, the first two characters identifying the hour, from 0 to 24, and the last two characters indicating the respective time in minutes, from 0 to 59. In the case of the time-correction dataset T, the data field B contains the amount by which the time was altered.

In the illustrated embodiment, the data field B of the time-correction dataset T contains the number of minutes by which the time was adjusted so that in the case of a time-correction dataset the data field B contains an entry between 0 and the maximum number of minutes contained in 24 hours, i.e. 1140. In principle, it is however also possible to enter in the respective position of the data field of a time-correction dataset the respective number of hours or minutes, in which case the first two digits of the data field B would indicate the number of hours by which the clock was adjusted, while the two last digits of the dataset B would indicate the number of minutes by which the minute value indicated by the clock was adjusted.

In the illustrated embodiment of the time-correction dataset T the clock of the hand-held device 1 was adjusted by 2 hours so that, correspondingly, the data field B shows the entry 0120 to indicate that the clock was adjusted by 120 minutes.

In the case of a measured value dataset the third data field C of the datasets indicates the date when the measured values were obtained, the first two digits indicating the year, the next two digits indicating the month, and the last two digits indicating the day in the illustrated embodiment. In the case of a time-correction dataset the last two digits may indicate the number of days by which the clock was adjusted, while the two digits before these last two digits indicate the number of months, and the first two digits indicate the number of years by which the respective part of the date was adjusted.

The fourth field D of the datasets of the embodiment discussed above contains different flags that indicate if the entries in data fields B and C of a time-correction dataset are positive or negative, thereby indicating the direction in which the clock setting was altered. For example, the character B in the dataset T indicates as a flag that the clock was set back. Preferably, the field D additionally contains a check bit or a check digit to allow a dataset to be checked for possible writing or reading errors. Additionally, the field D may contain an entry indicating whether the measured value of the respective measured value dataset is above or below a predefined threshold value.

The data field B of a measured value dataset is described as a time field in a measured value dataset and as a time-correction field in a time-correction dataset. Correspondingly, the data field C is described as a date field in a measured value dataset and as a date-correction field in a time-correction dataset.

When the clock is set it may happen that the amount by which the clock was adjusted cannot be determined. That case may arise for example when the device is started up for the first time or after an extended power failure, for example when the battery is replaced. In such a case, the control unit will write into the storage a special dataset, preferably of the same length and structure as the measured-value and the time-correction datasets. Such a special dataset can be distinguished from a time-correction dataset by a special marking that may be positioned in the flag field D, for example.

While the invention has been illustrated and described in detail in the drawings and foregoing description, the same is to be considered as illustrative and not restrictive in character, it being understood that all changes and modifications that come within the spirit of the invention are desired to be protected.

LIST OF REFERENCE NUMERALS

1 Hand-held device
2 Carrier strip
3 Display means
4 Operating element
5 Hardware interface
M1, M2, M3 Measured value dataset
T Time-correction dataset
A, B, C, D Data field

What is claimed is:

1. A method of processing a sequence of measured values for analyte concentrations in a hand-held device when time settings are changed in the hand-held device, the method comprising the steps of:
   providing in a measured-value storage of the hand-held device a date and an hour of day for each measured value in a sequence of measured values of an analyte concentration;
   generating in the measured-value storage a measured values dataset for each measured value in the sequence, wherein each measured value in the measured values dataset is assigned a plurality of data fields;
   providing in the measured-value storage a time change indicator of an amount of change in a time setting and a direction of change in the time setting when a clock of the hand-held device is changed;
   generating in the measured-value storage a time-correction dataset for each time change indicator, wherein each time change indicator is assigned the plurality of data fields;
   generating in the measured-value storage a chronological sequence of each measured values dataset and each time-correction dataset that are sorted in the measured-value storage according to time of generation; and
   optionally evaluating the chronological sequence.

2. The method of claim 1, wherein the plurality of data fields is four data fields.

3. The method of claim 2, wherein in the measured values dataset the four data fields are (1) an analyte concentration field, (2) an hour of day field, (2) a date field, and (4) a check field; and wherein in the time-corrected dataset the four data fields are (1) a time change indicator marking field, (2) an amount of change of time setting in minutes field, (3) an amount of change of time setting in at least one of days, months and years field, and (4) a direction of change of time setting field.

4. The method of claim 3, wherein the first data field, the second data field and the fourth data field each are four characters in length, and wherein the third data field is six characters in length.

5. The method of claim 3, wherein in the time-corrected dataset, the time change indicator marking field begins with a bit string that represents the character 9.

6. The method of claim 1, wherein the analyte concentration is a glucose concentration.

7. A method of managing a sequence of measured values for analyte concentrations in a hand-held analyte concentration measurement device when time settings are changed in the hand-held device, the method comprising the steps of:

providing in a measured-value storage of the hand-held device a date and an hour of day for each measured value in a sequence of measured values of an analyte concentration;

generating in the measured-value storage a measured value dataset each containing a plurality of data fields, wherein in one of these data fields one of the measured values of the sequence is stored and in at least one other of these data fields the date and/or the hour of day for this measured value is stored;

providing in the measured-value storage a time change indicator of an amount of change in a time setting and a direction of change in the time setting when a clock of the hand-held device is changed;

generating in the measured-value storage a time-correction dataset for each time change indicator, wherein each time change indicator is assigned the plurality of data fields;

generating in the measured-value storage a chronological sequence of each measured values dataset and each time-correction dataset that are sorted in the measured-value storage according to time of generation;

evaluating the chronological sequence by calculating a corrected time for the measured value datasets that are stored in the chronological sequence from the date and hour of day of the respective measured value data set and the time change indicator of the time-correction dataset or the time-correction datasets.

8. The method of claim 7, wherein the measured value datasets and the time-correction datasets have the same length.

9. The method of claim 7, wherein time-correction datasets are identified as time-correction datasets by a marking in the data field that contains the measured value of the measured value datasets.

10. The method of claim 9, wherein the marking of the time-correction datasets has the same length as the field of the measured value datasets that contains the measured value.

11. The method of claim 7, wherein the measured value datasets contain a data field that indicates the hour of the day when the measurement was taken and the time-correction datasets contain in that data field the time change indicator that indicates the number of minutes by which the hour of the day was changed by the changing of the clock.

12. The method of claim 7, wherein the time-correction datasets contain a data field that indicates the direction in which the clock was changed.

13. The method of claim 7, wherein a special dataset is generated in the measured-value storage when at the time the clock is set no reference time is available that would be altered by the changing of the clock and when, consequently, neither the amount nor the direction of the changing of the clock can be indicated.

* * * * *